United States Patent [19]

Liberman

[11] Patent Number: 4,840,035
[45] Date of Patent: Jun. 20, 1989

[54] METHOD OF FREEZING TISSUE

[75] Inventor: Barnet L. Liberman, 421 Hudson St., New York, N.Y. 10014

[73] Assignees: Barnet L. Liberman; Winthrop D. Chamberlain, both of New York; Joseph Fedele; Brian Fedele, both of Queens, all of N.Y. ; a part interest

[21] Appl. No.: 219,330

[22] Filed: Jul. 14, 1988

[51] Int. Cl.$^4$ ............................................. F25D 17/02
[52] U.S. Cl. ............................................ 62/64; 62/78; 426/524; 435/1
[58] Field of Search ..................... 62/64, 78; 435/1; 426/524

[56] References Cited

U.S. PATENT DOCUMENTS

| | | | |
|---|---|---|---|
| 4,059,967 | 11/1977 | Rowe et al. | 62/78 |
| 4,309,449 | 1/1982 | O'Roark et al. | 62/64 |
| 4,601,909 | 7/1986 | Nagoshi | 62/64 |
| 4,654,217 | 3/1987 | Nagoshi | 62/64 |
| 4,657,768 | 4/1987 | Nagoshi | 62/64 |
| 4,689,963 | 9/1987 | Sakai | 62/64 |

Primary Examiner—Ronald C. Capossela
Attorney, Agent, or Firm—Cohen, Pontani & Lieberman

[57] ABSTRACT

A method of freezing tissue samples for cytological or histological examination is provided. The method includes the steps of preparing a brine including cruciferous oil, cooling the brine, providing a tissue sample, and subjecting the tissue sample to the cooled brine for a period of time sufficient to freeze the tissue sample.

20 Claims, 1 Drawing Sheet

METHOD OF FREEZING TISSUE

BACKGROUND OF THE INVENTION

This invention relates generally to methods of freezing tissue and, in particular, to a method of freezing tissue samples to prevent deterioration of the cellular structure of the tissue or in preparation for immediate examination, with or without staining and fixing.

Methods of freezing tissue for cytological or histological examination are known and available. For example, freezing of tissues by cryogenic techniques using liquid nitrogen are relatively common, albeit expensive. Moreover, there may be damage to the cellular structure which interferes with a rapid and accurate examination of cryogenically frozen tissue.

A Method of Freezing Fishery Products is known from U.S. Pat. No. 4,601,909 issued to Nagoshi on July 22, 1986. This method includes the steps of preparing a brine containing rapeseed oil, propylene glycol, calcium chloride and water, cooling the brine and immersing the seafood in the cooled brine until it is frozen. This method reduces or eliminates breakdown of muscle tissue in the seafood. Hence, deterioration in quality of the frozen product is prevented or reduced.

A similar process for Quick Freezing of Meat is disclosed and claimed in U.S. Pat. No. 4,654,217 issued to the same inventor on Mar. 31, 1987. The process disclosed in this later patent is similar to that disclosed in the earlier patent except that it is applicable to beef, poultry, pork and the like.

U.S. Pat. No. 4,657,768 issued to Nagoshi on Apr. 14, 1987, discloses a Freezing Method for Perishable Foods which includes placing a perishable food in a heat conducting container and causing the other surface of the heat conducting container to contact cooled brine or a liquefied gas. Accordingly, the perishable food is frozen quickly without immersion.

U.S. Pat. No. 4,689,963 issued to Sakai on Sept. 1, 1987, relates to a Method of Freezing Foods. The method of Sakai is similar to the method of Nagoshi except that a layer of brine is placed in the heat conducting container along with the perishable food. Freezing proceeds only from the portion which is in contact with the brine and the potential for the food to stick to the container is reduced.

There is no teaching or suggestion in any of these patents that these processes can be used to freeze tissue samples for cytological or histological examination.

Accordingly, it is desirable to provide a process for freezing tissue samples for purposes of cytological or histological examination.

It is, therefore, an object of the invention to provide a process for quick freezing tissue samples for histological and cytological tissue examination.

A further object of the invention is to provide a method of freezing tissue samples which does not destroy the cellular structure of the sample.

Still another object of the invention is to provide an economical method of freezing tissue samples.

Still other objects and advantages of the invention will in part be obvious and will in part be apparent from the specification.

SUMMARY OF THE INVENTION

Generally speaking, in accordance with the invention, a method for freezing tissue for purposes of cytological or histological examination is provided. The method includes the steps of preparing a brine including a cruciferous oil; cooling the brine to a temperature between about $-22°$ and $-43.6°$ F.; providing a tissue sample; and subjecting the tissue sample to the cooled brine for a period of time sufficient to freeze the tissue sample. The brine generally includes a glycol, a salt and water in addition to the suitable oil.

The invention accordingly comprises the several steps and the relation of one or more of such steps with respect to each of the others thereof which will be exemplified in the method hereinafter disclosed and the scope of the invention will be indicated in the claims.

BRIEF DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENTS

Figure 1:
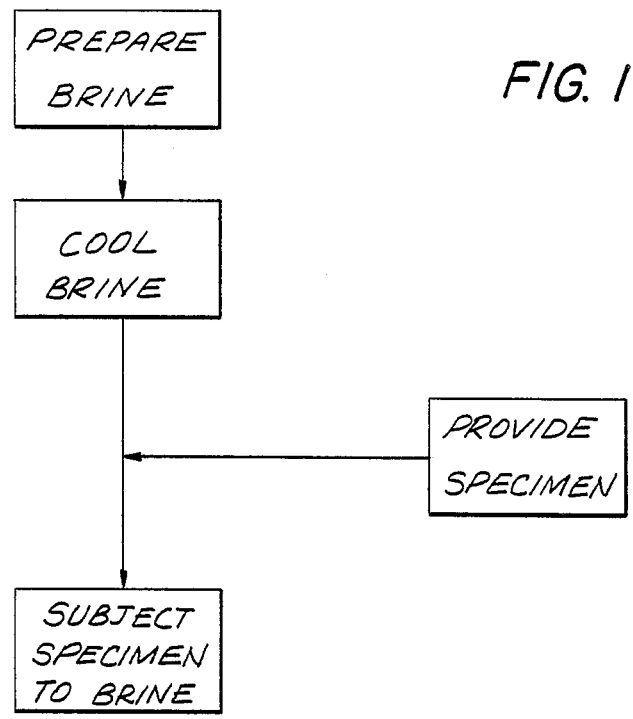
FIG. 1 is a flow diagram showing the method of the invention.

FIG. 1 is a flow diagram depicting the method of the invention. As shown, the method includes the steps of preparing a brine, cooling the brine, providing a specimen and subjecting the specimen to the colled brine.

The first step of the process of freezing tissue samples in accordance with the invention is preparation of a suitable brine solution which includes a cruciferous oil. In a preferred embodiment, oil from a plant of the genus Brassica is used. These oils include, but are not limited to, oil of *Brassica* campestris, otherwise known as rapeseed oil, and oil of *Brassica* hirta, also known as mustard oil.

Rapeseed oil has a solidification point of $-10°$ C., a specific gravity at 15° C. of 0.915, a refractive index at 50° C. of 1.4706, an iodine value of 98.6 and a saponification value of 174.7. The oil includes about 1% palmitic acid, the only saturated component of the oil, about 32% oleic acid, about 15% linoleic acid, about 1% linolenic acid and about 50% erucic acid. Palmitic acid, otherwise known as hexadecanoic acid is a saturated fatty acid having 16 carbon atoms and a molecular weight of 256.4.

Oleic acid, also known as (Z)-9-octadecenoic acid, has 18 carbon atoms and a molecular weight of 282.5. The position of unsaturation is between the ninth and tenth carbon atoms in the chain. The molecule has a cis configuration.

Linoleic acid has two positions of unsaturation and is also known as cis,cis-9,12-octadecadienoic acid. The acid has 18 carbon atoms and a molecular weight of 280.5.

Linolenic acid has three positions of unsaturation and is also known as (Z,Z,Z)-9,12,15-octadecatrienoic acid. Linolenic acid has 18 carbon atoms and a molecular weight of 278.4.

Erucic acid, a major component of the oils of the genus Brassica, is also known as (Z)-13-docosenoic acid. Erucic acid has 22 carbon atoms with one position of unsaturation and a molecular weight of 338.6.

Mustard oil is similar. Mustard oil has a specific gravity at 15° C. of 0.9145, a refractive index at 50° C. of 1.475, an iodine value of 102 and a saponification value of 174. Mustard oil includes 1.3% by weight myristic acid, the only saturated acid, 27.2% by weight oleic acid, 16.6% by weight linoleic acid, 1.8% by weight linolenic acid, 1.1% by weight behenic acid, 1.0% by weight lignoceric acid and 51.0% by weight erucic acid. Myristic acid, also known as tetradecanoic acid, has 14 carbon atoms and a molecular weight of 228.4.

Behenic acid is also known as docosanoic acid. It has 22 carbon atoms and a molecular weight of 340.6. Lignoceric acid, also known as tetracosanoic acid, has 24 carbon atoms and a molecular weight of 368.6. The other components of mustard oil are described above.

The oil is used in an amount less than about 1% by weight, more preferably less than about 0.8% by weight and most preferably between about 0.1 and 0.5% by weight of the brine.

It is to be understood that oils other than rapeseed oil and mustard oil can be used in accordance with the invention. For example, synthetic oils having the characteristics described would be useful. In addition, the manner in which the oils function is described in detail below and it will be readily apparent that other oils will function acceptably in accordance with the invention and can be readily determined.

In addition to the cruciferous oil, the brine also generally includes a glycol, an inorganic salt and water. Suitable glycols include, but are not limited to, ethylene glycol, propylene glycol, benzylene glycol, butylene glycol, diethylene glycol, diphenyl glycol, ethylidene glycol, and the like. Any glycol can be used alone or in combination with other glycols. Propylene glycol is used in a preferred embodiment. The glycol component is present in an amount between about 30 and 50% by weight of the brine, more preferably between about 35 and 45% by weight and most preferably in an amount of about 40% by weight.

Salts which are useful in accordance with the invention include, but are not limited to, calcium chloride, calcium bromide, calcium iodide, potassium chloride, potassium bromide, potassium iodide and the like. In a preferred embodiment, calcium chloride is used. The salt is present in an amount between about 5 and 15% by weight of the brine, more preferably in an amount between about 7 and 13% by weight and most preferably in an amount of about 10% by weight.

Water is present in an amount between about 40 and 60% by weight, more preferably in an amount between about 45 and 55% by weight and most preferably in an amount of about 50% by weight In an especially preferred embodiment, the brine has the following composition:

| Component | Amount (% by weight) |
|---|---|
| Cruciferous oil | 0.1–0.5 |
| Propylene glycol | 40 |
| Calcium chloride | 10 |
| Water | about 50 |

The cruciferous oil is preferably rapeseed oil, mustard oil or a mixture thereof.

It is currently believed that when the brine including the oil is cooled to a temperature between about $-22°$ and $-43.6°$ F., fine ice crystals form in the brine and are uniformly distributed. Assuming this belief to be true, then it is likely that these crystals will permit efficient cold transfer and an increase in the expected freezing rate of a tissue sample immersed in the brine. Consequently, the time required to freeze the tissue sample is reduced. In an especially preferred embodiment, cooling means are provided for removing heat from the brine so as to maintain the temperature of the brine at a substantially constant value when a tissue sample is introduced, thereby permitting the tissue sample to pass rapidly through the zone of maximum ice crystal formation, that is, between about $-0.5°$ and $-5°$ C. Accordingly, formation of ice crystals, breakdown of cellular tissue and deterioration of the sample is minimized.

Prior to freezing, the tissue samples are prepared by known techniques. Suitable tissue samples may be of plant or animal origin. The tissue samples are preferably thin sheets of, for example, lungs, liver, eyes, hearts and the like, although chunklike specimens may be frozen and examined, especially after being cut into thin slices as by a microtome. The tissue samples are frozen by immersing in the brine for a period of between about ½ and 2 minutes. In an alternate method, which is useful in accordance with the invention, the tissue can be frozen by placement in a heat-conducting pan or tray. The opposite side of the pan or tray is then placed in contact with the cooled brine described. In a further alternate embodiment, brine is placed in the heat-conducting pan or tray and then the opposite side of the tray is placed into contact with the cooled brine in order to freeze the tissue samples.

Figure 2:
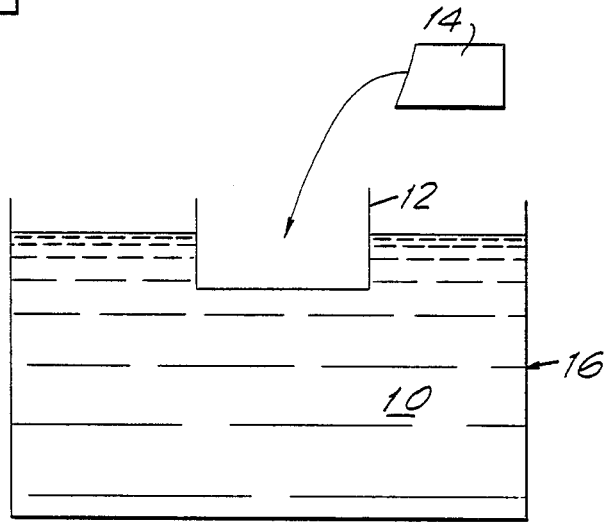
FIG. 2 is a cross-sectional plan view of an apparatus for use in performing the method of the invention.

FIG. 2 shows an apparatus for carrying out the method of the invention wherein a brine 10 is contained within a suitable container 16. A tissue specimen 14 is provided in a heat transfer pan 12. Heat transfer pan 12 is shown in contact with brine 10 so that tissue specimen 14 in heat transfer pan 12 can be frozen in accordance with the method of the invention. In an alternate embodiment, a small amount of brine is placed inside heat transfer pan 12 along with tissue specimen 14 in order to facilitate the rapid freezing of tissue specimen 14.

After freezing, the tissue can be examined. The samples are particularly useful because damage to the cellular structure is minimized using the process described.

The frozen specimen must then be sliced as by a microtome into thin sheets for microscopic examination. The method of freezing tissue samples is believed to be especially useful because removal of water and cross-linking of molecules is minimized.

It will thus be seen that the objects set forth above, among those made apparent from the preceding description, are efficiently attained and, since certain changes may be made in carrying out the above method without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly, it is to be understood that in said claims, ingredients of compounds recited in the singular are intended to include compatible mixtures of such ingredients wherever the sense permits.

What is claimed is:

1. A method of freezing a tissue specimen comprising:
   preparing a brine including at least about 0.1% by weight of a cruciferous oil;
   cooling the brine to a temperature between about $-22°$ and $-43.6°$ F.;
   providing a tissue specimen; and subjecting the tissue specimen to a heat transfer relationship with the cooled brine for a period of time sufficient to freeze the tissue specimen.

2. The method of freezing tissue of claim 1, wherein the oil is extracted from a plant of the genus Brassica.

3. The method of freezing tissue of claim 1, wherein the oil is selected from the group consisting of rapeseed oil, mustard oil and mixtures thereof.

4. The method of freezing tissue of claim 1, wherein the oil contains erucic acid as the single largest component.

5. The method of freezing tissue of claim 1, wherein the oil contains less than about 2% saturated components.

6. The method of freezing tissue of claim 1, wherein the oil is used in an amount between about 0.1 and 0.5% by weight of the brine.

7. The method of freezing tissue of claim 1, wherein the brine further includes a glycol, an inorganic salt and water.

8. The method of freezing tissue of claim 7, wherein the glycol is propylene glycol.

9. The method of freezing tissue of claim 7, wherein the glycol is present in an amount between about 30 and 50% by weight of the brine.

10. The method of freezing tissue of claim 7, wherein the salt is calcium chloride.

11. The method of freezing tissue of claim 7, wherein the salt is present in an amount between about 5 and 15% by weight of the brine.

12. The method of freezing tissue of claim 7, wherein the water is present in an amount between about 40 and 60% by weight of the brine.

13. The method of freezing tissue of claim 1, wherein the tissue specimen is a thin sheet of a plant or animal material.

14. The method of freezing tissue of claim 1, wherein the tissue specimen is brought into a heat transfer relationship with the brine for a period between about ½ and 2 minutes.

15. The method of freezing tissue of claim 1, wherein the tissue specimen is subjected to a heat transfer relationship by immersion of the tissue specimen in the cooled brine.

16. The method of freezing tissue of claim 1, wherein the tissue specimen is subjected to a heat transfer relationship by placing the specimen in a heat transfer pan and subjecting the heat transfer pan to the cooled brine.

17. The method of freezing tissue of claim 1, wherein the tissue specimen is subjected to a heat transfer relationship by placing the specimen into a heat transfer tray along with sufficient brine to at least coat the bottom of the tray and subjecting the heat transfer tray to the cooled brine.

18. A method of freezing a tissue specimen comprising:
preparing a brine including an effective amount of a suitable oil for increasing the freezing rate of a tissue specimen brought into a heat transfer relationship therewith so as to minimize deterioration in the cellular structure of the specimen;
cooling the brine to a temperature between about $-22°$ and $-43.6°$ F.;
providing a tissue specimen; and
subjecting the tissue specimen to a heat transfer relationship with the cooled brine for a period of time sufficient to freeze the tissue specimen.

19. A method of freezing a tissue specimen of claim 18, wherein the brine includes between about 0.1 and 1.0% by weight of a cruciferous oil selected from the group consisting of rapeseed oil, mustard oil and mixtures thereof.

20. A method of freezing a tissue specimen of claim 18, wherein the brine further includes between about 30 and 50% by weight propylene glycol, between about 5 and 15% by weight calcium chloride and a balance of water.

* * * * *